US00PP20385P2

(12) United States Plant Patent
Oliver

(10) Patent No.: US PP20,385 P2
(45) Date of Patent: Oct. 6, 2009

(54) *HEUCHERA* PLANT NAMED 'CRYSTAL SPIRES'

(50) Latin Name: *Heuchera×hybrida*
Varietal Denomination: Crystal Spires

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 12/154,221

(22) Filed: May 21, 2008

(51) Int. Cl.
*A01H 5/00* (2006.01)

(52) U.S. Cl. ..... Plt./440

(58) Field of Classification Search ..... Plt./440
See application file for complete search history.

*Primary Examiner*—June Hwu
(74) *Attorney, Agent, or Firm*—C. A. Whealy

(57) ABSTRACT

A new and distinct cultivar of *Heuchera* plant named 'Crystal Spires', characterized by its full, densely foliated and uniformly mounded plant habit; vigorous growth habit; silver-colored upper leaf surfaces and purple-colored lower leaf surfaces; numerous large white-colored flowers arranged on erect panicles; and excellent garden performance.

2 Drawing Sheets

Botanical designation: *Heuchera×hybrida.*
Cultivar denomination: 'Crystal Spires'.

BACKGROUND OF THE INVENTION

The present invention relates to a new and distinct cultivar of *Heuchera,* botanically known as *Heuchera×hybrida* and hereinafter referred to by the name 'Crystal Spires'.

The new *Heuchera* is a product of a planned breeding program conducted by the Inventor in Scottdale, Pa. The objective of the breeding program is to create new vigorous *Heuchera* cultivars with uniform plant habit, and attractive leaf and flower coloration.

The new *Heuchera* originated from a cross-pollination made by the Inventor on Jun. 23, 2001 in Scottdale, Pa. of *Heuchera* 'Raspberry Ice', disclosed in U.S. Plant Pat. No. 13,340, as the female, or seed, parent with *Heuchera* 'White Queen', not patented, as the male, or pollen, parent. The new *Heuchera* was discovered and selected by the Inventor as a single flowering plant within the progeny of the stated cross-pollination in a controlled greenhouse environment in Scottdale, Pa. in May, 2003.

Asexual reproduction of the new *Heuchera* by cuttings in a controlled greenhouse environment in Scottdale, Pa. since March, 2004, has shown that the unique features of this new *Heuchera* are stable and reproduced true to type in successive generations.

SUMMARY OF THE INVENTION

The new *Heuchera* has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Crystal Spires'. These characteristics in combination distinguish 'Crystal Spires' as a new and distinct cultivar of *Heuchera:*

1. Full, densely foliated and uniformly mounded plant habit.
2. Vigorous growth habit.
3. Silver-colored upper leaf surfaces and purple-colored lower leaf surfaces.
4. Numerous large white-colored flowers arranged on erect panicles.
5. Excellent garden performance.

Plants of the new *Heuchera* differ from plants of the female parent, 'Raspberry Ice', in the following characteristics:

1. Plants of the new *Heuchera* have rounded leaf lobes whereas plants of 'Raspberry Ice' have jagged leaf lobes.
2. Plants of the new *Heuchera* have larger flowers than plants of 'Raspberry Ice'.
3. Flowers of plants of the new *Heuchera* have larger petals than flowers of plants of 'Raspberry Ice'.

Plants of the new *Heuchera* differ from plants of the male parent, 'White Queen', in the following characteristics:

1. Leaves of plants of the new *Heuchera* are more silvery in color than leaves of plants of 'White Queen'.
2. Plants of the new *Heuchera* have shorter inflorescences than plants of 'White Queen'.
3. Flowers of plants of the new *Heuchera* have longer, but narrower petals than flowers of plants of 'White Queen'.

Plants of the new *Heuchera* can be compared to plants of the *Heuchera* 'Silver Scrolls', disclosed in U.S. Plant Pat. No. 12,066. In side-by-side comparisons conducted in Scottdale, Pa., plants of the new *Heuchera* differed from plants of 'Silver Scrolls' in the following characteristics:

1. Plants of the new *Heuchera* had shorter and broader inflorescences than plants of 'Silver Scrolls'.
2. Plants of the new *Heuchera* were more freely flowering than plants of 'Silver Scrolls'.
3. Plants of the new *Heuchera* had longer flowers than plants of 'Silver Scrolls'.

4. Flowers of plants of the new *Heuchera* had larger petals than flowers of plants of 'Silver Scrolls'.

Plants of the new *Heuchera* can also be compared to plants of the *Heuchera* 'Harmonic Convergence', disclosed in U.S. Plant Pat. No. 11,111. In side-by-side comparisons conducted in Scottdale, Pa., plants of the new *Heuchera* differed from plants of 'Harmonic Convergence' in the following characteristics:

1. Plants of the new *Heuchera* had more erect inflorescences than plants of 'Harmonic Convergence'.
2. Plants of the new *Heuchera* had larger flowers than plants of 'Harmonic Convergence'.

BRIEF DESCRIPTION OF THE PHOTOGRAPHS

The accompanying colored photographs illustrate the overall appearance of the new *Heuchera,* showing the colors as true as it is reasonably possible to obtain in colored reproductions of this type. Colors in the photographs may differ slightly from the color values cited in the detailed botanical description which accurately describe the colors of the new *Heuchera.*

The photograph on the first sheet comprises a side perspective view of a typical plant of 'Crystal Spires'.

The photograph on the second sheet is a close-up view of a typical inflorescence of 'Crystal Spires'.

DETAILED BOTANICAL DESCRIPTION

The aforementioned photographs and following observations, measurements and values describe plants grown in Scottdale, Pa. in one-gallon containers in a glass-covered greenhouse and under conditions which closely approximate commercial *Heuchera* production. During the production of the plants, day temperatures ranged from 15° C. to 26° C. and night temperatures ranged from 5° C. to 15° C. Plants were one year old when the photographs and the description were taken. In the description, color references are made to The Royal Horticultural Society Colour Chart, 1995 Edition, except where general terms of ordinary dictionary significance are used.

Botanical classification: *Heuchera×hybrida* 'Crystal Spires'.

Parentage:

*Female, or seed, parent.*—*Heuchera×hybrida* 'Raspberry Ice', disclosed in U.S. Plant Pat. No. 13,340.

*Male, or pollen, parent.*—*Heuchera×hybrida* 'White Queen', not patented.

Propagation:

*Type.*—By cuttings.

*Time to initiate roots, summer.*—About 15 days at 23° C.

*Time to initiate roots, winter.*—About 21 days at 17° C.

*Time to produce a rooted young plant, summer.*—About 45 days at 23° C.

*Time to produce a rooted young plant, winter.*—About 60 days at 17° C.

*Root description.*—Fine, fibrous; white in color.

*Rooting habit.*—Freely branching; moderately dense.

Plant description:

*Appearance.*—Herbaceous perennial; basal rosette plant habit with leaves developing from the base; densely foliated; full, mounded and uniform plant habit with upright panicles with white-colored flowers. Vigorous growth habit.

*Plant size.*—Height, soil level to top of foliar plane: About 20 cm. Height, soil level to top of panicles: About 50 cm. Diameter or spread: About 40 cm.

Foliage description:

*Arrangement.*—Basal rosette, simple.

*Length.*—About 7 cm.

*Width.*—About 6 cm.

*Shape.*—Rounded cordate; seven-lobed.

*Apex.*—Broadly obtuse, lobed.

*Base.*—Auriculate.

*Margin.*—Crenate with ciliation.

*Texture, upper and lower surfaces.*—Slightly pubescent; slightly rough.

*Venation pattern.*—Palmate; reticulate.

*Color.*—Developing leaves, upper surface: Close to 198C, underlain with close to 187B. Developing leaves, lower surface: Close to 187B. Fully expanded leaves, upper surface: Close to 198C; venation, close to 189A, underlain with close to 200A. Fully expanded leaves, lower surface: Close to 187B; venation, close to 187B.

*Petioles.*—Length: About 12 cm. Diameter: About 2 mm. Texture, upper and lower surfaces: Smooth. Color, upper and lower surfaces: Close to 187C, underlain with close to 138D.

Flower description:

*Appearance/arrangement.*—Single flared campanulate flowers arranged on loose, narrow and mostly erect panicles; about ten to 20 panicles develop during the flowering season, each panicle with about 80 to 125 flowers and flower buds. Flowers face mostly outward to slightly downward. Flowers not fragrant.

*Time of flowering.*—Plants flower from May through June in Scottdale, Pa., flowering continuous during this period.

*Inflorescence longevity.*—Individual inflorescences last about one week on the plant. Flowers persistent.

*Inflorescence size.*—Length: About 50 cm. Diameter: About 4 cm.

*Flower size.*—Diameter: About 5 mm. Depth (height): About 8 mm.

*Flower buds.*—Height: About 5 mm. Diameter: About 3 mm. Shape: Bulbous. Color: Close to 155D; towards the apex, shaded with close to 150D; towards the base, shaded with close to 185D.

*Sepals.*—Quantity/arrangement: Five sepals; radially symmetrical and fused at base. Calyx length: About 7 mm. Calyx diameter: About 5 mm. Shape: Elongate. Apex: Obtuse. Margin: Entire. Texture, upper and lower surfaces: Pubescent. Color, upper surface: Close to 155D; scattered glandular hairs, close to 59C. Color, lower surface: Close to 155D; towards the apex, shaded with close to 150D; towards the base, shaded with close to 185B.

*Petals.*—Quantity/arrangement: Five minute petals; radially symmetrical. Length: About 3.5 mm. Width: About 1.6 mm. Shape: Spatulate. Apex: Acute. Margin: Serrate. Texture, upper surface: Smooth, glabrous. Texture, lower surface: Glandular hairs. Color, upper surface: Close to 155D. Color, lower surface: Close to 155D; glandular hairs, close to 59C.

*Flower bracts.*—Length: About 1.4 mm. Width: About 0.2 mm. Shape: Lanceolate. Apex: Acute. Margin: Serrate. Texture, upper and lower surfaces: Glandular hairs. Color, upper and lower surfaces: Close to 187B.

*Peduncles.*—Strength: Strong. Aspect: Mostly erect to about 30° from vertical. Length: About 30 cm to 40 cm. Diameter: About 2 mm. Texture: Pubescent. Color: Close to 187B.

*Pedicels.*—Strength: Strong. Aspect: About 45° from vertical. Length: About 2.5 mm. Diameter: About 0.2 mm. Texture: Pubescent. Color: Close to 187B.

*Reproductive organs.*—Androecium: Stamen number: Five per flower. Anther shape: Oval. Anther size: About 0.6 mm by 0.5 mm. Anther color: Close to 12A. Amount of pollen: Scarce. Pollen color: Close to 12A. Gynoecium: Pistil number: Two per flower. Pistil length: About 6 mm. Stigma shape: Round. Stigma color: Close to 157A. Style length: About 5 mm. Style color: Close to 157A. Ovary color: Close to 157A.

*Seed.*—Size: About 0.6 mm by 0.3 mm. Color: Close to 202A.

Disease/pest resistance: Resistance to pathogens and pests common to *Heuchera* has not been observed on plants grown under commercial conditions.

Garden performance: Plants of the new *Heuchera* have been observed to have excellent garden performance. Plants of the new *Heuchera* have demonstrated good tolerance to rain, wind, night temperatures as low as −30° C. and day temperatures as high as 45° C.

It is claimed:

1. A new and distinct *Heuchera* plant named 'Crystal Spires' as illustrated and described.

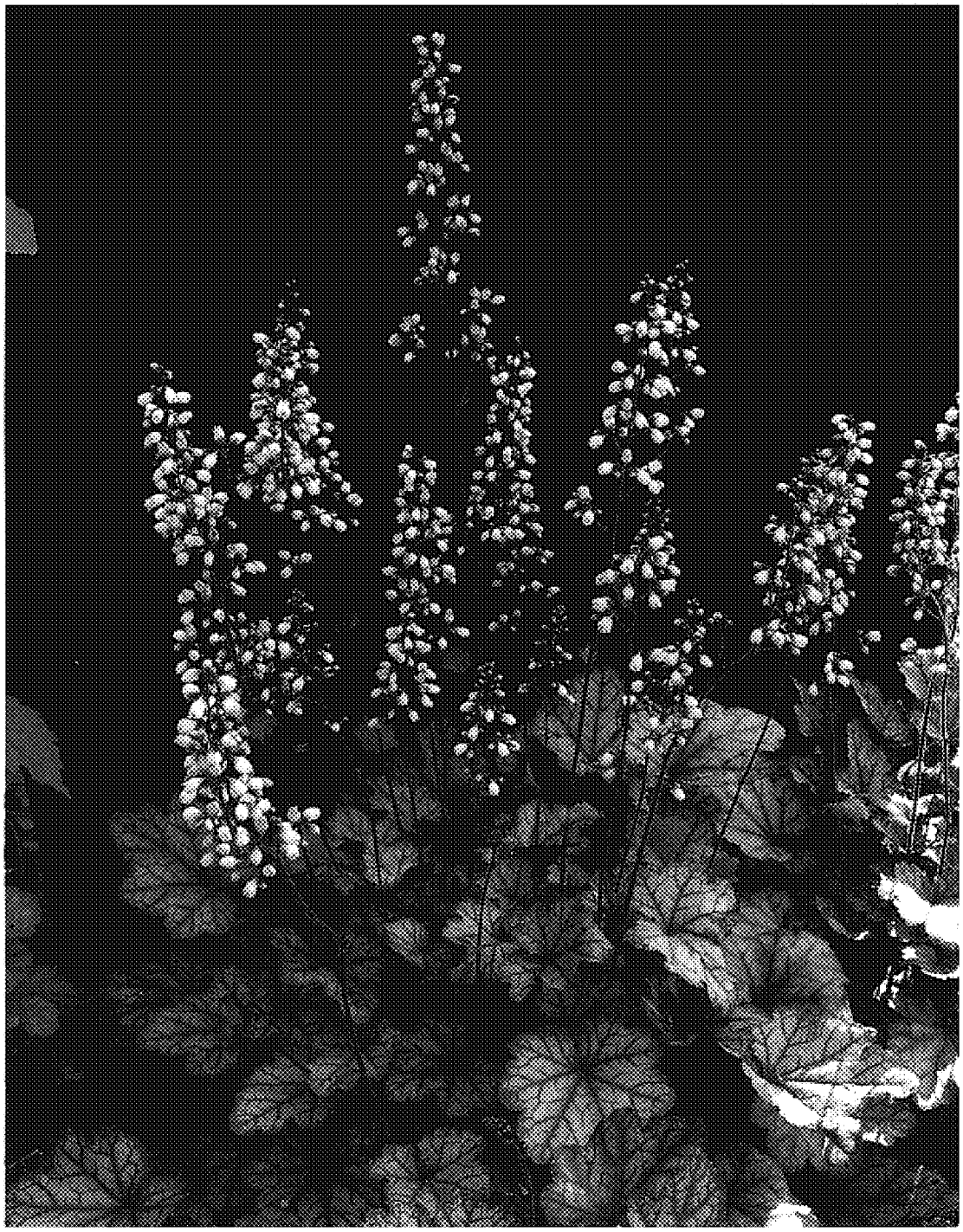

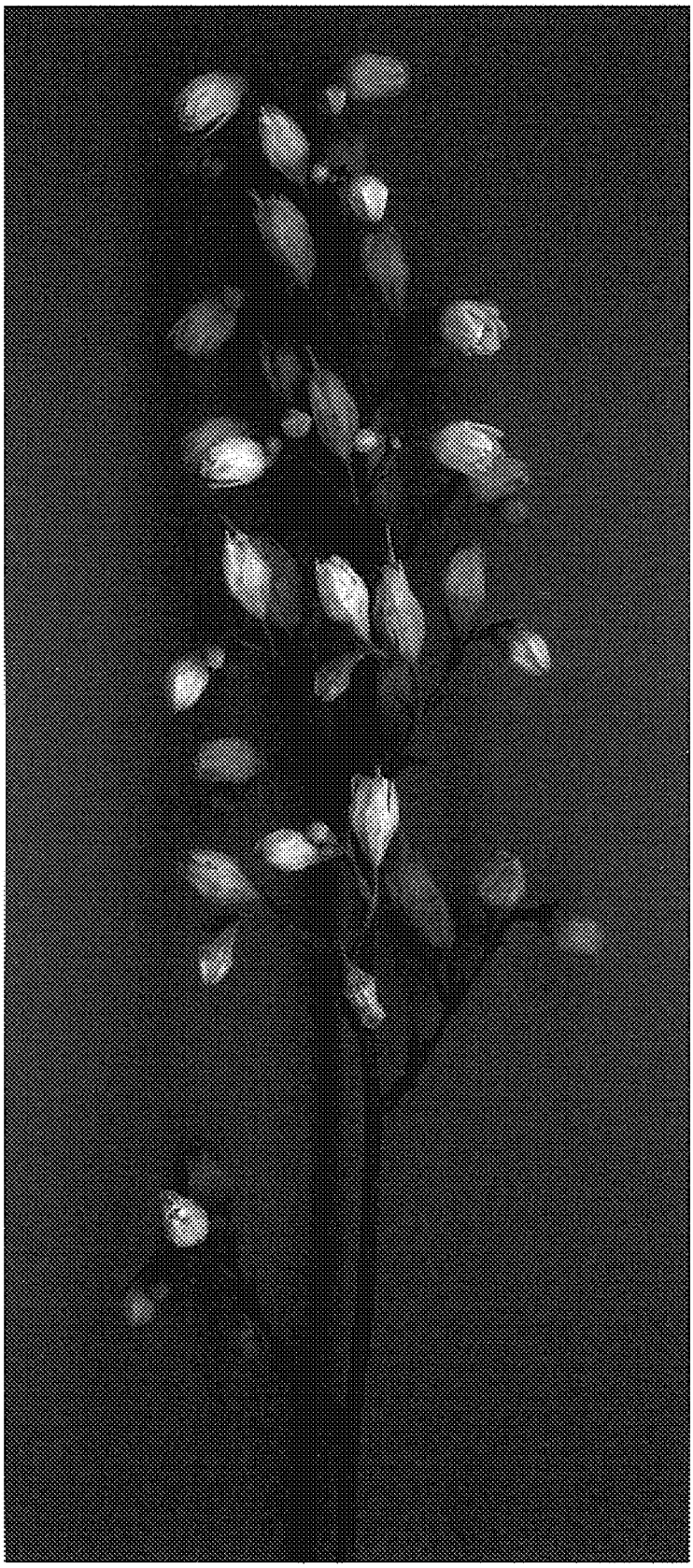

* * * * *